United States Patent [19]

Meyer

[11] Patent Number: 5,131,382

[45] Date of Patent: Jul. 21, 1992

[54] ENDOSCOPIC PERCUTANEOUS DISCECTOMY DEVICE

[76] Inventor: William F. Meyer, 773 Trotter Ct., Walnut, Calif. 91789

[21] Appl. No.: 328,952

[22] Filed: Mar. 27, 1989

[51] Int. Cl.$^5$ .............................................. A61B 1/00
[52] U.S. Cl. ........................................ 128/6; 604/22; 606/170
[58] Field of Search ................ 604/21, 22; 128/4-6, 128/305; 606/170

[56] References Cited

U.S. PATENT DOCUMENTS

| | | | |
|---|---|---|---|
| 1,150,214 | 8/1915 | London | 606/170 |
| 1,675,364 | 7/1928 | Loeck | 128/4 |
| 3,618,611 | 11/1971 | Urban | 128/305 |
| 3,791,379 | 2/1974 | Storz | 128/4 |
| 4,146,019 | 3/1979 | Bass et al. | 128/6 |
| 4,203,444 | 10/1977 | Bonnell | 128/276 |
| 4,300,870 | 1/1983 | Vukovic | 128/6 |
| 4,343,300 | 8/1982 | Hattori | 128/6 |
| 4,487,489 | 12/1984 | Takamatsu | 128/6 |
| 4,550,716 | 11/1985 | Kimoshita | 128/6 |
| 4,598,710 | 7/1986 | Kleinberg et al. | 128/751 |
| 4,601,284 | 7/1986 | Arakawa et al. | 128/6 |
| 4,607,621 | 8/1986 | Wheeler | 128/6 |
| 4,637,142 | 10/1986 | Buess et al. | 128/6 |
| 4,678,459 | 7/1987 | Onik et al. | 604/22 |
| 4,708,126 | 11/1987 | Toda et al. | 128/6 |
| 4,715,332 | 4/1988 | Heckele | 128/6 |
| 4,756,309 | 7/1988 | Sachse et al. | 128/6 |
| 4,756,708 | 7/1988 | Martin | 604/93 |
| 4,759,348 | 7/1988 | Cawood | 128/6 |
| 4,791,913 | 12/1986 | Maloney | 128/6 |
| 4,869,768 | 1/1989 | Reid, Jr. | 128/6 |

Primary Examiner—C. Fred Rosenbaum
Assistant Examiner—William Lewis

[57] ABSTRACT

A system of energy form generating and transmitting devices that allow direct visualization during removal of disc tissue material from the human body discs which are located between vertebrae of the back, during percutaneous discectomy. Energy form generators are controlled and coordinated within a modularized console. Energy form transmitters are placed partially within the disc and are coordinated in the same physical structure to minimize size.

A coordinated system of surgical devices which create a space in the disc (21), (71), (172), illuminate the disc space (20), (120), removed disc material (21), (71), (122), under direct visual control from the posterior aspect of the disc (134), (128), and provide a means for transporting debris (22), (23), (172), (166), (78), from the disc during the surgical procedure.

A system of energy form generating and energy transmitting surgical devices which function in an integrated manner to provide illumination, visualization, tissue resection, and transport of resected tissue, from an area of the body which not normally a body cavity.

10 Claims, 3 Drawing Sheets

ENDOSCOPIC PERCUTANEOUS DISCECTOMY DEVICE

BACKGROUND

1. Field of the Invention

This invention relates to a system of products which are used to remove herniated or protruding disc material from the human body back using a surgical technique which involves making a very small incision through the skin into the lower back, endoscopic percutaneous discectomy. This typical embodiment is a specific example of a system of products which permit visualization into an area of the human body which is not a normal body cavity, and then under direct visual control, removal of abnormal or pathological structures from that portion of the body.

2. Description of Prior Art

Normal method for surgical treatment of a severely bulging or herniated disc in the lower back is massive open surgery in which an 8-10 inch incision in the skin is made, followed by dissection down through muscles and ligaments to access the actual disc, that is only 3-5 cubic centimeters in volume. Pain, suffering, and extended time to complete recovery is caused much more by the 8-10 inch surgical incision or wound. Time for return to a normal lifestyle is 4-6 months following this operation, according to published medical papers. National cost for this operation, including both cost of actual medical care and workman's compensation from the extended time off from work is about $3 billion annually.

A more recently employed operation involves "microsurgery" in which only a 2-3 inch skin incision is made, to reduce pain, time in the hospital immediately following surgery, and time for return to normal. Within the last 2-3 years, percutaneous discectomy, a surgical procedure in which tubes are placed through the skin and into the disc, and a portion of the disc is removed, using manual instruments or a pneumatically powered cutting device, has been used by a limited number of pyhsicians. The theory behind the percutaneous discectomy procedure is, if disc material is removed, pressure within the disc will be reduced and the herniation from the disc will retract into the main portion of the disc.

Success rate for percutaneous discectomy has only been about 70%, much lower than for the major, 8-10 inch surgical operation, and a cause and effect relationship for failure of percutaneous discectomy has not been proven. But since percutaneous discectomy, an operation that can be performed on an outpatient basis, involves much less pain, suffering, recovery time, and cost, it has become more popular with surgeons and patients, and a lower success rate, 70%, is an acceptible complication. If initial percutaneous discectomy is unsuccessful, reoperation or the open surgical procedure is performed.

This has benefitted the nation as a whole, given the explosive increase in cost of medical care which this country is currently experiencing. Since disabling back injury is increasing faster than any other injury, since compensable back injuries affect 2% of all employees each year, and since 24% of all lost time industrial accidents are back related, according to Federal government statistics, improved devices used to perform percutaneous discectomy are needed, to provide a higher success rate and further reduce the cost in treating this specific medical problem.

Prior art involves open tubes placed into the disc, through which manually operated stainless steel surgical instruments are passed. These instruments bite off chunks of the disc material which are then enclosed in the instrument. The instrument must be removed from the back to clean out the material and then be reinserted into the back, repeating this technique many times to excise a sufficient enough volume of disc material to have positive effect.

Additional prior art is a system of devices for percutaneous discectomy involving open tubes placed into the disc, through which a pneumatically powered cutting device is passed. This product also aspirates excised material from the disc, and collects it in a volume measuring reservoir.

Although these devices effectively remove some disc material, lack of visual control during the removal process and more importantly lack of visual control to ascertain completeness of the excision dictates the operating physician must rely on measure of volume of excised material to assume that enough has been removed to produce a positive effect and relieve the symptoms of the patient.

Biomechanical studies suggest that removal of disc material from the anterior portion of the disc space, which is dictated by the design of the prior art, produces a far less stable post-surgery lower back, and may be a contributing factor to a high failure rate for the prior art.

Because of size of prior art, pneumatically powered cutting devices, removal of adequate volume of disc material is a tedious process for the surgeon, and extends time of surgery, and as a result cost of medical care. Use of prior art products leaves a dead space in the back which immediately fills with fluid and eventually loose connective tissue. Preferrably, bone should fill this space, as is done during the major, open surgical procedure, when insertion of bone graft material to create what is known as a spinal fusion is one of the final phases of the procedure.

Related prior art involves small diameter, optical medical telescopes which have been used for orthopaedic arthroscopy for several year, and other surgical procedures for decades. Arthroscopes have a shape and size that make them beneficial in performing the arthroscopic technique, but not effective for performing percutaneous discectomy.

Additonal related prior art is fiber optic light illuminators that are used for medical, endoscopic surgical procedures in general and for orthopaedic arthroscopy in particular. These light sources do not provide the light intensity to properly illuminate the disc space, and produce clear images with the medical video camera system that is used in conjuction with the percutaneous discectomy scope.

Additional related prior art is a peristaltic pump used to instill fluid, usually normal saline, into a body cavity to expand its volume, and provide a clear liquid medium to view the body cavity using a generic type of endoscope. This instilled fluid may be removed from the body cavity either through the endoscope or through a separate outflow conduit, usually by applying active suction to the conduit and connecting PVC tubing, the suction being generated by some external aspirating pump. Precise control of rate of inflow is not achieved with prior art instilling pumps, and coordination of volume of inflow to volume of aspiration, through electronic controls is not characteristic of these forms of prior art.

Related prior art are machines which function independently including light source illuminators, peristaltic pumps, pneumatically powered tissue resectors, suction machines, and electromechanical tissue resectors used for surgical procedures other than indicated in this patent application.

As indicated above, a system of devices for percutaneous discectomy is a typical embodiment of a generic system of energy form generating and energy form transmitting surgical devices which function in an integrated, coordinated manner to provide illumination, visualization, tissue resection, and transport of resected tissue, from an area of the human body which is not normally a body cavity, With the aspect of the system that is placed partially within the human body containing all energy forms within the same physical structure, and with the energy generating or energy transforming aspect of the system contained in the same chasis.

Prior art for the generic system of energy form generating and energy form transmitting surgical devices are energy form generators that produce light to illuminate a body cavity such as the stomach, lung, bladder, or abdomen, energy form generators that produce electrical cutting energy used through an energy transporting device to remove abnormal tissue such as from the stomach, intestine, or urinary tract, electromechanical energy cutting devices used through an energy transporting device to remove abnormal tissue such as from the knee, shoulder, or blood vessel system, energy form generators that produce laser cutting energy used through an energy transporting device to remove abnormal tissue such as from the intestine, blood vessel system, cranium, abdomen, or lung.

Additional related prior art is indicated above, specifically endoscopes which are used to visualize within body cavities, and pumps and aspiratiang devices which are used to inflow and aspirated fluids into and out of these body cavities.

Prior art devices are not designed to coordinate all four functions identified in this invention, illumination, visualization, energy form generation and transmission, and transport medium inflow and outflow, within the same operating console, and within the same device that is placed partially within the human body, but not into a normal body cavity. Therefore, these devices do not work as efficiently together, extend operating time which increases cost of medical care. Energy form generators and transporters being separate machines, their total cost is greater ands they require more effort by personnel to set up and maintain, which also increases cost of medical care. Because several separate devices must be placed within the human body with prior art devices, multiple surgical incisions are required which increases recovery time, pain and suffering for the patient.

OBJECTS AND ADVANTAGES

Objects and advantages of the machine described in the present invention are:

(a) to provide a medical telescope which permits the surgeon to view within the lumbar disc space of the human body back to observe disc material, incorporating in this component of the machine a means to accomodate a disc material removing device that can be positioned to remove the material from the most posterior aspect of the disc space, maintaining optical control of the disc removing process to assure that the process completely removes material from the portion of the space which is most biomechanically effective in treating the patients condition and resulting in the most stable condition for the lumbar spine after the operation has been completed, also incorporating in this component of the machine a means to allow inflow and aspiration of a transporting medium to maintain clear visualization and effective extraction of debris created by the disc removing process, obviating the need to perform major open surgery which involves extensive hospital stay, extended time to complete recovery, and much higher cost for both direct medical care and workman's compensation, while using a device which provides greater control of the disc removal process than can be achieved with products that do not allow direct visual control of the disc removal process, do not permit disc removal from the portion of the disc which produces the best biomechanical result, and which do not possess a disc material transporting mechanism to reduce operating time;

(b) to provide a means to allow insertion of the medical telescope and disc material removing devices into the lumbar disc, which is small diameter, and therefore easily inserted by the operating physician without excessive pain for the patient during the procedure, obviating the need for the surgeon to make a major incision into the back which in the past has resulted in considerably more pain, extensive hospital stay, extended time to complete recovery, and much higher cost of medical care;

(c) to provide a means of support for the disc material removing component, within the medical telescope, allowing the disc material removing component to function properly, and protecting the optical component of the medical telescope from damage during this process;

(d) to provide a means for instilling fluid into the disc, to move debris away from the end of the medical telescope and thereby maintain clear visualization, lubricate the disc removing component if necessary, and also provide a vehicle for transport of debris created during the disc removal process, to the outside of the body;

(e) to provide a more efficient, more cost effective, easily operated energy source to create and/or deliver into the disc the proper form of energy that is used to actually perform the disc removal process, reducing operating time while being able to remove a clinically significant amount of disc material;

(f) to provide a means for removing the disc material from the posterior portion of the disc, which results in a more stable post-operative condition for the back and which may, as a result, increase the success rate of the endoscopic percutaneous discectomy procedure;

(g) to provide a very high intensity light source as component of the system, which generates appropriate forms and quantity of light sufficient to properly illuminate and/or differentiate structures within the disc for observation, when a small size video camera is attached to the proximal end of an appropriately small diameter medical telescope;

(h) to provide a means for controlled inflow of fluid into and aspiration of fluid from the disc to maintain clear viewing of the disc during the procedure and efficient transport of debris which is created during removal of disc material from the back;

(i) to provide an interrelated and coordinate system of energy sources within the same physical chasis including light source, energy source to remove disc material, and energy source to inflow and control aspiration of a transporting medium, with the chasis modularized for efficient service.

Further objects and advantages are to provide a system of devices which will permit the surgeon to remove disc material from the lumbar disc during endoscopic percutaneous discectomy under direct visualization so that disc material is completely removed from the optimal position within the disc, obviating the need to perform major open surgery while producing a success rate equal to open surgery, reducing pain and discomfort for the patient, reducing hospital stay, reducing time to complete recovery, and reducing cost for medical care. The system will be relatively inexpensive in comparison to prior art which also contributes to lower cost for medical care. Still further objects and advantages will become apparent from a consideration of the ensuing description and drawings.

DESCRIPTION OF THE PREFERRED EMBODIMENT

Figure 1:
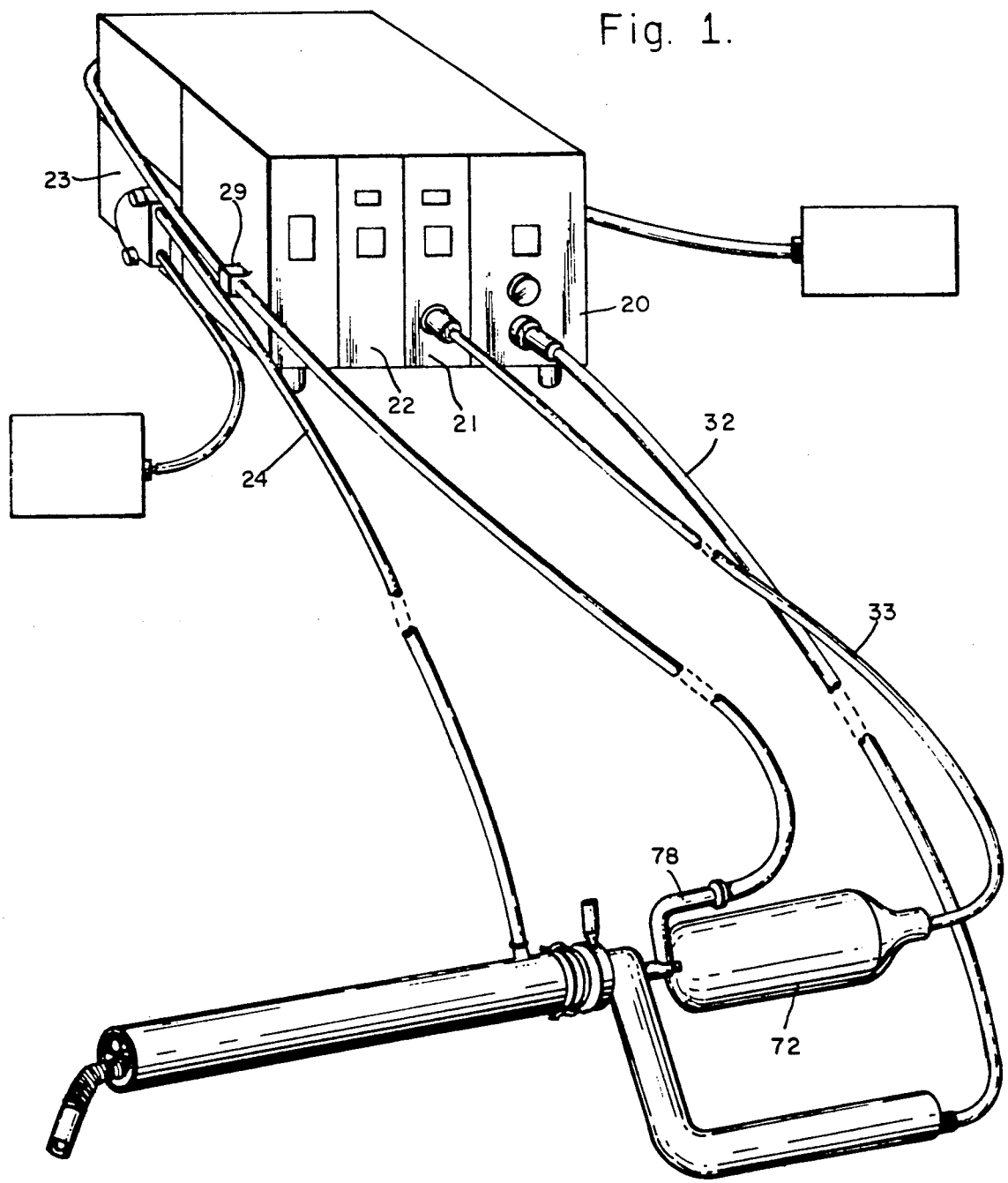
FIG. 1 is a perspective drawing of the endoscopic resecting sytem which includes a console and a endoscopic viewing and resecting apparatus and which has been made in accordance with the principles of the preferred embodiment of the present invention.

In order to best understand the present invention it is necessary to refer to the following description of its preferred embodiment in conjunction with the accompanying drawing. Referring to FIG. 1 an endoscopic resecting system includes a console and an endoscopic viewing and resecting apparatus for viewing and resecting a target tissue such as a herniated intervertebral disc. The console includes at least four separate modules which are a light source module 20, a motor module 21, a transport medium pump control 22, and transport medium peristaltic pump module 23. On the front side of the light source module 20 are its operating controls which include an on/off toggle power switch, a light source intensity digital read-out, an intensity adjusting rheostat, and a fiber optic cable connection. On the front side of the motor module 21 are its operating controls which include an on/off toggle power switch, a motor speed adjustment, and a motor handpiece connection. The electronic components of the motor module 21 include a connection to a 110 volt external power supply, an on/off toggle power switch, a printed circuit board, a transformer, a heat sink, a speed adjusting control and motor handpiece connection. The console which is electrically coupled to a 110 volt external power supply, also includes an on/off toggle power switch, a power supply, a lamp, a lamp cooling fan, a digital read-out of intensity, and a protecting glass and a light intensity measuring device. The non-electronic components of the console also include support brackets for the power supply, the rheostat used to adjust light intensity, the aperature plate, the light attenuator, the fiber optic cable holder and the lourves near the lamp and in line with air flow from the fan.

Still referring to FIG. 1 on the front side of the transport medium pump controls module 22 are its operating controls which include an on/off inflow pump and suction control toggle switch, an inflow rate digital read-out, and inflow rate adjusting rheostat and a suction pressure adjusting rheostat. On the side of the transport medium pumps controls module 22 is a suction tube occluding device 29 which regulates suction pressure from a suctioning apparatus. The tube occluding device 29 is adjusted to regulate the outflow of the saline and the resected tissue from the surgical site. The transport medium pump controls module 22 includes a connection to a 110 volt external power supply, an on/off toggle power switch, an inflow rate digital read-out, an inflow rate adjusting rheostat, a printed circuit board for the pump and controls, a printed circuit board for the suction controls, and a suction pressure adjusting rheostat. On the side of the peristaltic pump module 23 is a pump tubing holder which is mechanically coupled to inflow tubing 24. A saline source is fluidly coupled to the inflow tubing 24. The electronic components of the peristaltic pump module 23 include a connection to pump controls module, a transformer and a motor. The non-electronic conmponents of the peristaltic pump module 23 include a system of torque dampeners, a pump driver, the peristaltic action producing wheel and a mechanical connector from motor shaft to peristaltic action producing wheel.

Figure 2:
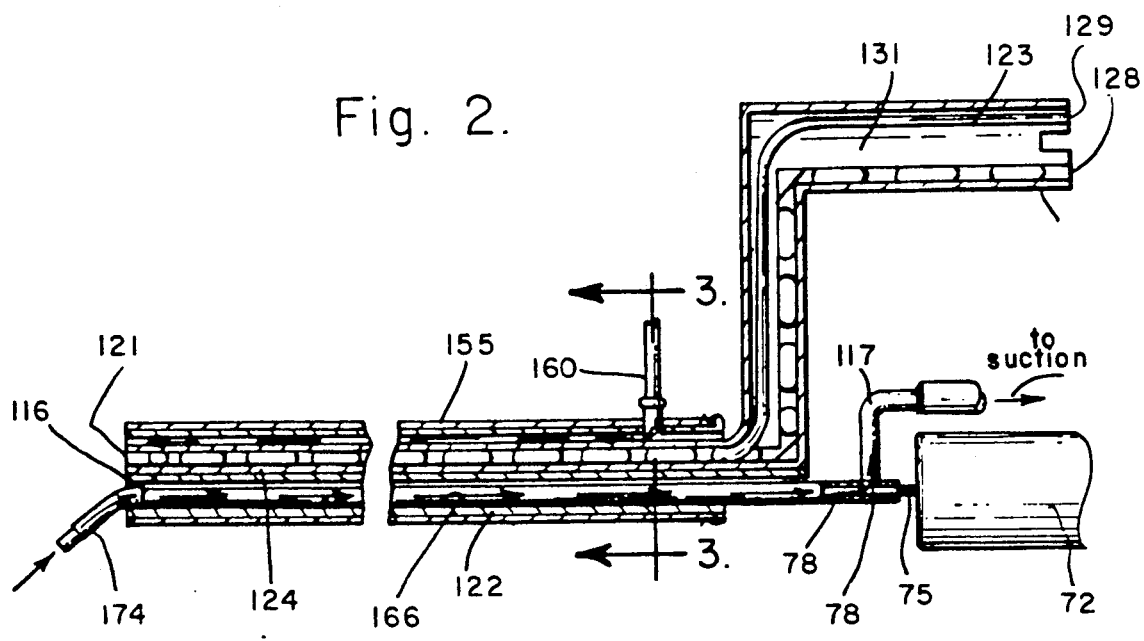
FIG. 2 is a partial longitudinal cross-sectional view of the endoscopic viewing and resecting apparatus of FIG. 1 which includes a sleeve, a visualizing device, and illuminating device and a resecting mechanism.
Figure 3:
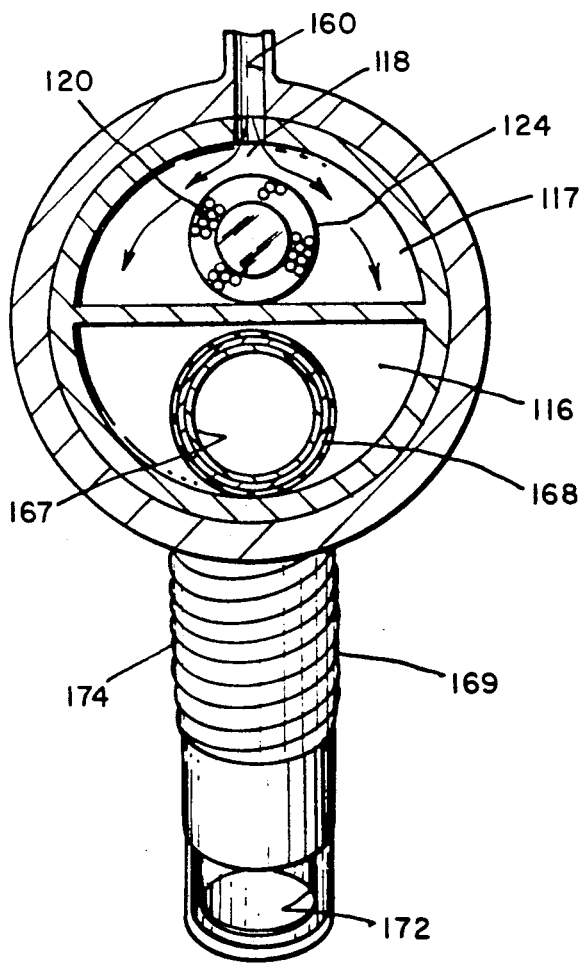
FIG. 3 is a transverse cross-sectional view of the endoscopic viewing and resecting apparatus of FIG. 1 taken along the line 3—3 of FIG. 2 which also includes a compartmentalized tube, an irrigating apparatus and an aspirating outflow apparatus.
Figure 4:
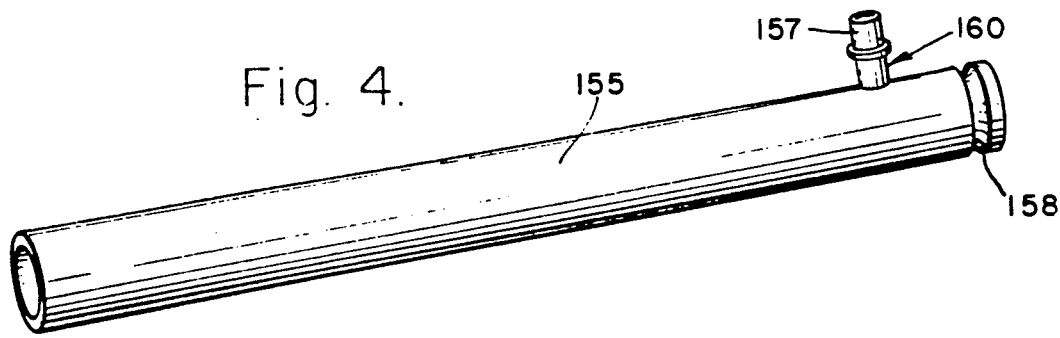
FIG. 4 is a perspective drawing of the sleeve of the endoscopic viewing and resecting apparatus of FIG. 1 into which the compartmentalized tube is inserted.

Referring to FIG. 2 in conjunction with FIG. 1 and 3 the endoscopic viewing and resecting apparatus includes a compartmentalized tube 155, a visualizing device 131, an illuminating device 124, a resecting mechanism 174, an irrigating apparatus 160, and an aspirating apparatus 110. The suctioning apparatus which is provided in the operating room is fluidly coupled to the aspirating apparatus 110. The irrigating apparatus 160 has an inflow connector 118 which is mechanically coupled to the compartmentalized tube near its proximal end and which is fluidly and mechanically coupled to the saline source by the inflow tubing 24.

Figure 5:
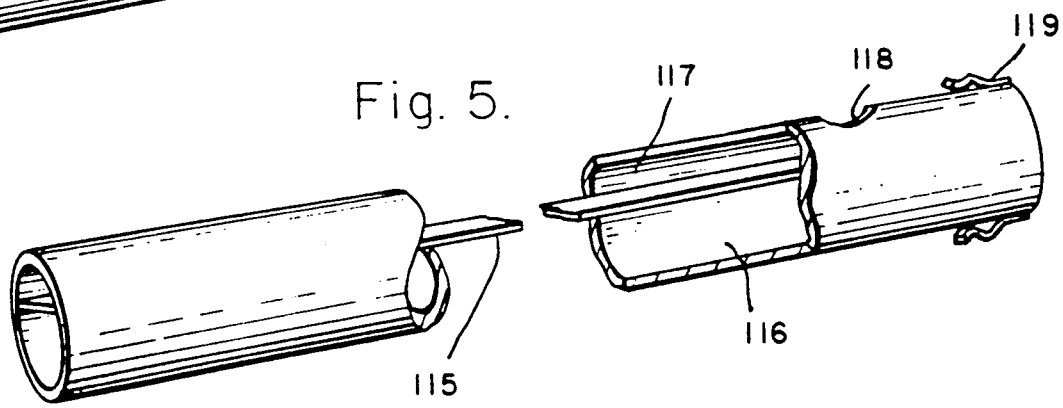
FIG. 5 is a partial perspective drawing of the compartmentalized tube of the endoscopic viewing and resecting apparatus of FIG. 1.

Referring to FIG. 5 in conjunction with FIG. 2 and FIG. 3 the compartmentalized tube 155 has a first compartment 117 of a first set of dimensions, a second compartment 116 of a second set of dimensions larger than the first set of dimensions, and a barrier 115 between the first and second compartments. The visualizing device 131 directly views the target tissue. A portion of the visualizing device 131 is disposed in the first compartment 117. The illuminating device 124 provides illumination of the target tissue. A portion of the illuminating device 124 is disposed in the first compartment 117. The resecting mechanism 174 resects the target tissue. A portion of the resecting mechanism 174 is disposed in the second compartment 116. The inlet 160 inlets a transport fluid to the resected target tissue. The outlet 110 outlets the transport fluid to a suctioning device. A portion of the outlet 110 is disposed in the second compartment 116. The visualizing device 131, the illuminating device 124, the resecting mechanism 174, the inlet 160, and the outlet 110, all function is an integrated and coordinated manner.

The visualizing device 131 includes a hollow metal sheath 123 and an eyepiece 128. A portion of the hollow metal sheath 123 is disposed in the first compartment 117. The eyepiece 128 is mechanically and optically coupled to the hollow metal sheath 123 at its proximal end. The visualizing device 131 includes a lens train and a focusing lens 121. The lens train has a plurality of lenses and is mechanically and optically coupled to the eyepiece 128 and disposed in the hollow metal sheath 123. The focusing lens 121 is mechanically and optically coupled to the lens train and disposed in the hollow metal sheath 123 at its distal end. A small video camera may be attached to the eyepiece 124. The illuminating mechanimsm 120 includes an optical fiber and a light generator. A portion of the optical fiber is disposed within the metal sheath 123 parallel to the lens train and is optically aligned with the lens train. U.S. Pat. No. 4,601,284, entitled Endoscope Connecting System, issued to Satoshi Arakawa and David H. Cooper on Jul. 22, 1986, teaches a video camera which is optically coupled to an eyepiece, an optical-fiber connector which is disposed orthogonally to the eyepiece and a optical fiber. This is the standard arrangement of the prior art because the optical fiber needed to be out of the way of the surgeon's eye during endoscopy. Most endoscopy is now performed with a video monitor. In the present invention the eyepiece 128 and illuminating mechanism 120 are disposed contiguously and parallel to one another so that a single cable bundle to the console may be used. The light generator 21 generates light and is mechanically and optically coupled to the illuminating mechanism 120. The illuminating mechanism 120 provides illumination of the target tissue. A portion of the illuminating device 120 is disposed in the first compartment 117. The visualizing device 131, the illuminating device 120, the resecting mechanism 174, the irrigating apparatus 160 and the aspirating apparatus 110 all function in an integrated and coordinated manner.

Figure 6:
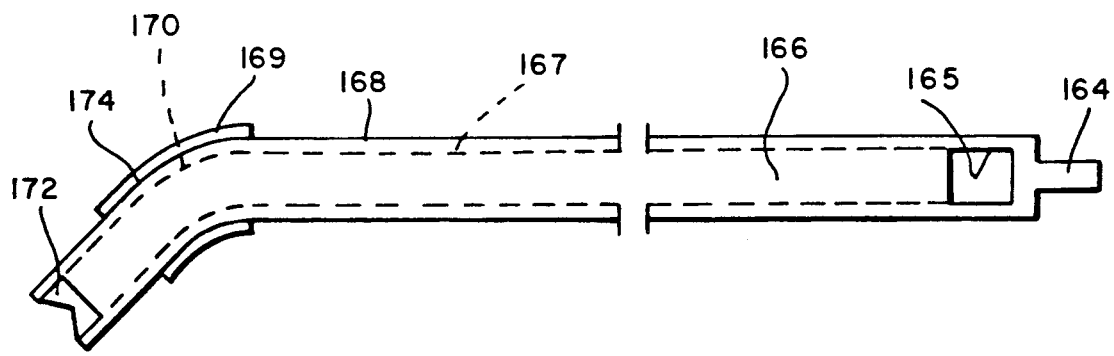
FIG. 6 is a longitudinal, cross-sectional view of the perferred embodiment of the disc material removing mechanism.

Referring to FIG. 6 in conjunction with FIG. 3 and FIG. 5, the resecting mechanism 174 may include a hollow tube 166 and a driving mechanism 164, or an outer tube 168, an inner tube 167, and driving mechanism 164. The hollow tube 166 has a proximal end and a distal end and is disposed in the second compartment 116. The hollow tube 166 has an open distal end and a cutting blade 172 just proximal to the open distal end. The hollow tube 166 has a window 165 near its proximal end. The driving mechanism 164 rotatively drives the hollow tube 166 so that the cutting blade 172 resects the target tissue. The resected target tissue and the transport medium are then aspirated into the the hollow tube 166 at the open distal end of the hollow tube 166 and then move through the lumen of the hollow tube 166 to the window 165 near the proximal end of the hollow tube 166. The outer tube 168 has a proximal end and a distal end and is disposed in the second compartment 116. The outer tube 168 has a slot with a peripheral edge at its distal end. The inner tube 167 has a proximal end and a distal end and is disposed coaxially with and rotatively coupled to the outer tube 168. The outer tube 168 has a spiral, flexible portion 174 which is covered by a plastic material 169. The inner tube 167 has a second slot with a second peripheral edge at its distal end and a window 165 at its proximal end. The inner tube 167 has a spiral, flexible portion 170. The driving mechanism 164 rotatively drives the inner tube 167 so that the first and second peripheral edges articulate thereby resecting the target tissue. The resected target tissue and transport medium are then aspirated into the lumen of the inner tube 167 at the second slot near the distal end of the inner tube 167. The target tissue moves through the lumen of the inner tube 167 to the window 165 near the proximal end of the inner tube. The driving mechanism 164 includes an electric motor 72 and a power cord 33 the distal end of which is connected to the motor module 21. The window 165 is disposed adjacent to the outlet connector 78.

Accordingly, the endoscopic resecting system can be used to remove a target tissue such as a herniated disc. All of the energy sources for illumination, target tissue removal, and transportation of debris are conveniently located in the same modularized console so that these processes of the operation are controlled and coordinated. The components of the endoscopic resecting system placed partially within the body are organized in order to minimize the outer diameter of the compartmentalized tube 155 while still coordinating all of these functions to efficiently and quickly complete the target tissue removal process.

Direct visual control of the target tissue removal process reduces the need to make large incisions into the body which in turn reduces pain, suffering, and surgical morbidity and also reduces the cost of direct medical care and the overall cost while patients recover from an open operation.

From the foregoing it can be seen that an endosopic resecting system has been described. It should be noted that the sketches are not drawn to scale and that distance of and between the figures are not to be considered significant.

I claim:

1. An endoscopic resecting system for viewing and resecting a target tissue, said endoscopic resecting system comprising:
    a. a compartmentalized hollow tube with a first compartment of a first set of dimensions and a second compartment of a second set of dimensions larger than said first sets of dimensions;
    b. visualizing means for directly viewing the target tissue, a portion of said visualizing means being disposed in said first compartment;
    c. illuminating means for providing illumination of the target tissue, a portion of said illuminating means being disposed in said first compartment;
    d. resecting means for resecting the target tissue, a portion of said resecting means being disposed in said second compartment;
    e. inletting means for inletting said transport fluid to said resected target tissue, a portion of said inletting means being disposed in said first compartment; and
    f. outletting means for outletting said transport fluid to the suctioning device, a portion of said outletting means being disposed in said second compartment whereby said visualizing means, said illuminating means, said resecting means, said inletting means and said outletting means all function in an integrated and coordinated manner.

2. An endoscopic resecting system for viewing and resecting a target tissue according to claim 1 wherein said visualizing means comprises:
   a. a hollow metal sheath which has a proximal end and a distal end and a portion of which is disposed in said first compartment;
   b. an eyepiece which is mechanically and optically coupled to said hollow metal sheath at its said proximal end, said eyepiece being disposed at an angle and adjacent to said resecting means;
   c. a lens train which has a plurality of lenses and which is mechanically and optically coupled to said eyepiece and disposed in said hollow metal sheath; and
   d. a focusing lens which is mechanically and optically coupled to said lens train and disposed in said hollow metal sheath at its said distal end.

3. An endoscopic resecting system for viewing and resecting a target tissue according to claim 2 wherein said illuminating means comprises:
   a. an optical fiber a portion of which is disposed within said hollow metal sheath and which is optically aligned with said lens train; and
   b. a light generating means for generating light which is mechanically and optically coupled to said optical fiber.

4. An endoscopic resecting system for viewing and resecting a target tissue according to claim 1 wherein said visualizing means comprises:
   a. a hollow metal sheath which has a proximal end and a distal end and a portion of which is disposed in said first compartment;
   b. an eyepiece which is mechanically and optically coupled to said hollow metal sheath at its said proximal end, said eyepiece being disposed at an angle and adjacent to said resecting means;
   c. a coherent optical fiber which is mechanically and optically coupled to said eyepiece and disposed in said hollow metal sheath; and
   d. a focusing lens which is mechanically and optically coupled to said coherent optical fiber and disposed in said hollow metal sheath at its said distal end.

5. An endoscopic resecting system for viewing and resecting a target tissue according to claim 4 wherein said illuminating means comprising:
   a. an optical fiber a portion of which is disposed within said hollow metal sheath and which is optically aligned with said coherent optical fiber; and
   b. a light generating means for generating light which is mechanically and optically coupled to said optical fiber.

6. An endoscopic resecting system for viewing and resecting a herniated intervertebral disc, said endoscopic resecting system comprising:
   a. a compartmentalized hollow tube with a first compartment of a first set of dimensions and a second compartment of a second set of dimensions larger than said first sets of dimensions;
   b. visualizing means for directly viewing the herniated intervertebral disc, a portion of said visualizing means being disposed in said first compartment;
   c. illuminating means for providing illumination of the herniated intervertebral disc, a portion of said illuminating means being disposed in said first compartment;
   d. resecting means for resecting a portion of the herniated intervertebral disc, said resecting means being disposed in said second compartment;
   e. inletting means for inletting a transport fluid to said resected herniated intervertebral disc, said inletting means being disposed in said first compartment; and
   f. outletting means for outletting said transport fluid to the suctioning device, a portion of said outletting means being disposed in said second compartment whereby said visualizing means, said illuminating means, said resecting means, said inletting means and said outletting means all function in an integrated and coordinated manner.

7. An endoscopic resecting system for viewing and resecting a herniated intervertebral disc according to claim 6 wherein said visualizing means comprises:
   a. a hollow metal sheath which has a proximal end and a distal end and a portion of which is disposed in said first compartment;
   b. an eyepiece which is mechanically and optically coupled to said hollow metal sheath at its said proximal end, said eyepiece being disposed at an angle and adjacent to said resecting means;
   c. a lens train which has a plurality of lenses and which is mechanically and optically coupled to said eye piece and disposed in said hollow metal sheath; and
   d. a focusing lens which is mechanically and optically coupled to said lens train and disposed in said hollow metal sheath at its said distal end.

8. An endoscopic resecting system for viewing and resecting a herniated intervertebral disc according to claim 7 wherein said illuminating means comprises:
   a. an optical fiber a portion of which is disposed within said hollow metal sheath and which is optically aligned with said lens train; and
   b. a light generating means for generating light which is mechanically and optically coupled to said optical fiber.

9. An endoscopic resecting system for viewing and resecting a herniated intervertebral disc according to claim 6 wherein said visualizing means comprises:
   a. a hollow metal sheath which has a proximal end and a distal end and a portion of which is disposed in said first compartment;
   b. an eyepiece which is mechanically and optically coupled to said hollow metal sheath at its said proximal end, said eyepiece being disposed at an angle and adjacent to said resecting means;
   c. a coherent optical fiber which is mechanically and optically coupled to said eyepiece and disposed in said hollow metal sheath; and
   d. a focusing lens which is mechanically and optically coupled to said coherent optical fiber and disposed in said hollow metal sheath at its said distal end.

10. An endoscopic resecting system for viewing and resecting a herniated intervertebral disc according to claim 9 wherein said illuminating means comprises:
   a. an optical fiber a portion of which is disposed within said hollow metal sheath and which is optically aligned with said coherent optical fiber; and
   b. a light generating means for generating light which is mechanically and optically coupled to said optical fiber.

* * * * *